US010420485B2

(12) United States Patent
Chung et al.

(10) Patent No.: US 10,420,485 B2
(45) Date of Patent: Sep. 24, 2019

(54) METHOD FOR ACQUIRING A VASCULAR WALL IMAGE FROM MAGNETIC RESONANCE IMAGING

(71) Applicants: GACHON UNIVERSITY OF INDUSTRY-ACADEMIC COOPERATION FOUNDATION, Seongnam-si (KR); GIL MEDICAL CENTER, Incheon (KR)

(72) Inventors: Jun Young Chung, Incheon (KR); Eung Yeop Kim, Incheon (KR)

(73) Assignees: GACHON UNIVERSITY OF INDUSTRY-ACADEMIC COOPERATION FOUNDATION, Seongnam-si (KR); GIL MEDICAL CENTER, Incheon (KR)

( * ) Notice: Subject to any disclaimer, the term of this patent is extended or adjusted under 35 U.S.C. 154(b) by 286 days.

(21) Appl. No.: 15/319,150

(22) PCT Filed: Mar. 26, 2015

(86) PCT No.: PCT/KR2015/002985
§ 371 (c)(1),
(2) Date: Dec. 15, 2016

(87) PCT Pub. No.: WO2015/194744
PCT Pub. Date: Dec. 23, 2015

(65) Prior Publication Data
US 2017/0119275 A1    May 4, 2017

(30) Foreign Application Priority Data
Jun. 18, 2014  (KR) ........................ 10-2014-0074443

(51) Int. Cl.
*A61B 5/055*    (2006.01)
*A61B 5/02*    (2006.01)
(Continued)

(52) U.S. Cl.
CPC .......... *A61B 5/055* (2013.01); *A61B 5/02007* (2013.01); *A61B 5/0263* (2013.01);
(Continued)

(58) Field of Classification Search
CPC .. G01R 33/5602; G01R 33/5635; G06T 5/50; G06T 2207/10088; G06T 2207/20224; G06T 2207/30101
See application file for complete search history.

(56) References Cited

U.S. PATENT DOCUMENTS

2010/0160767 A1   6/2010  Deimling
2010/0228115 A1*  9/2010  De Leon ................ A61B 5/055
                                                           600/410
(Continued)

FOREIGN PATENT DOCUMENTS

JP    2002-028149 A    1/2002
JP    2002-209867 A    7/2002
(Continued)

OTHER PUBLICATIONS

Steady-State MR Image Sequences: Physics, Classification and Clinical Applications, RadioGraphics 2008; 28: 1147-1160 to Shroff et al. (Year: 2008).*

*Primary Examiner* — Paula J Stice
(74) *Attorney, Agent, or Firm* — Seed IP Law Group LLP

(57) ABSTRACT

Images where the vascular walls are automatically divided are obtained by obtaining two MRI images that reflect different properties of the blood vessel and obtaining the difference between the two images. This can image both the vascular inner and the outer walls, thereby obtaining the exact size of the blood vessel, and the thickness between the vascular inner and outer walls. Therefore, it is possible to stably perform the operation using a stent with an accurate size during the stent procedure.

9 Claims, 3 Drawing Sheets

(51) Int. Cl.
*A61B 5/026* (2006.01)
*G01R 33/00* (2006.01)
*G01R 33/56* (2006.01)
*G01R 33/563* (2006.01)
*G06T 5/50* (2006.01)

(52) U.S. Cl.
CPC ......... *G01R 33/00* (2013.01); *G01R 33/5602* (2013.01); *G01R 33/5635* (2013.01); *G06T 5/50* (2013.01); *G06T 2207/10088* (2013.01); *G06T 2207/20224* (2013.01); *G06T 2207/30101* (2013.01); *G06T 2207/30104* (2013.01)

(56) References Cited

U.S. PATENT DOCUMENTS

| | | |
|---|---|---|
| 2010/0280357 A1 | 11/2010 | Bi et al. |
| 2012/0046541 A1 | 2/2012 | Wheaton |
| 2015/0302572 A1* | 10/2015 | Georgeson ............ G06T 7/0004 382/202 |

FOREIGN PATENT DOCUMENTS

| | | |
|---|---|---|
| JP | 2009-534116 A | 9/2009 |
| KR | 10-2010-0125884 A | 12/2010 |
| WO | 2013/057697 A1 | 4/2013 |

* cited by examiner

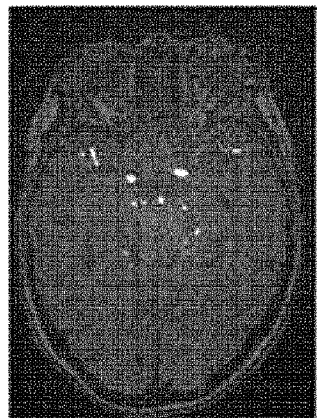 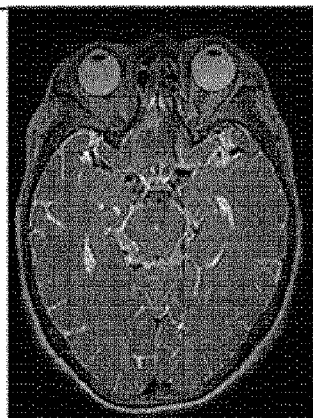 
FIG. 1(a) TOF Angio  FIG. 1(b) T2 weighted  FIG. 1(c) CISS T2/T1 weighted
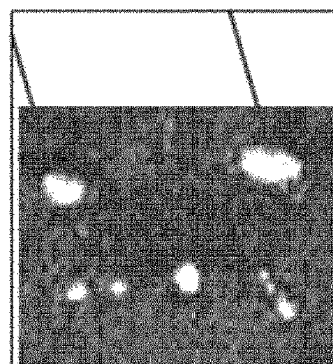 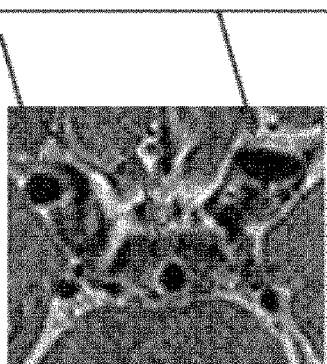 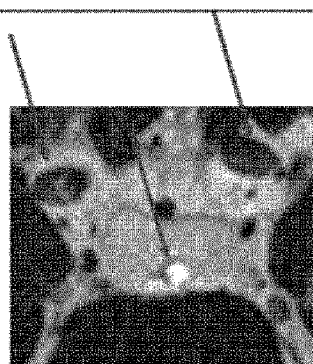
FIG. 2(a) TOF Angio  FIG. 2(b) T2 weighted  FIG. 2(c) CISS T2/T1 weighted

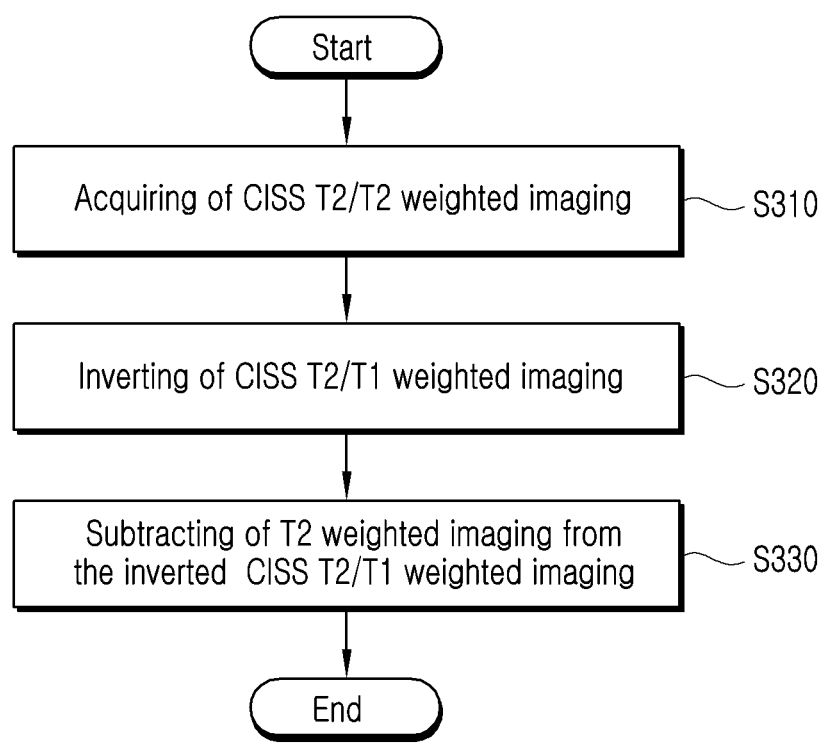
[Fig. 3]

METHOD FOR ACQUIRING A VASCULAR WALL IMAGE FROM MAGNETIC RESONANCE IMAGING

TECHNICAL FIELD

The present invention relates to an imaging technique implemented by an MRI (Magnetic Resonance Imaging) system, and more specifically to a method for acquiring an image in which vascular walls are automatically divided by using multimodal MRI imaging.

BACKGROUND ART

Diagnostic imaging methods include devices utilizing a variety of techniques such as X-ray, CT, ultrasonic, RI imaging, or MRI. Among them, MRI is the least harmful to the human body as compared with the other diagnostic imaging devices and forms images of the constituents in the human body. Hence, MRI is a very important device in clinical practice.

MRI devices can obtain tissue parameters such as spin density, T1, T2, chemical shift, magnetic transition, chemical exchange saturation transfer, blood flow, or spectroscopy which are unique information of the living body. Various biometric information images can also be obtained through such parameters.

Magnetic Resonance Angiography (MRA) is a method for measuring a blood flow in the arteries and veins of the human body using the MRI device and reconstituting the measured blood flow as an image. The MRA is currently providing clinical information which is very important for the diagnosis and treatment of vascular diseases. In the case of MRA imaging, there are various methods that utilize the properties of the blood flow rate, (i.e., TOF (time of flight)) using T1-weighted imaging of the blood flow.

Magnetic resonance angiography (MRA) imaging acquired by using an MRI device can measure the phenomenon caused by the blood flow through the blood vessels.

However, this connotes a probability that the blood flow rate can be changed by the vascular inner wall structure.

Furthermore, since X-Ray angiography inserts a catheter in the blood vessel and then administers a contrast agent, there is a fundamental problem in that the thickness of the blood vessel cannot be measured.

The thickness measurement of the brain vascular wall helps to objectively measure the progress of arteriosclerosis of a patient. As such, this can play a significant role in finding the causes of cerebral infarction and in the prevention of a future recurrence thereof. Therefore, there is a need for a method able to obtain an accurate thickness measurement of the vascular wall of the brain.

Current magnetic resonance imaging techniques for the vascular wall, which are used to observe the vascular wall, suppress the cerebrospinal fluid signal in the area through which blood flow pass and the area outside the blood vessel. Since the tunica media in the vascular inner wall has a dark signal if imaged with the magnetic resonance imaging system, conventional magnetic resonance imaging techniques for the vascular wall are not able to observe such a site. According to conventional techniques, only the thickness of the tunica adventitia can be measured and, consequently accurate vascular wall thickness cannot be measured. If the signal of the blood flow were to be separately obtained, together with a technique capable of imaging the tunica media site, it is expected that this would compensate for such disadvantages.

Accordingly, if it is possible to image both the vascular inner and outer walls to automatically divide them, it is possible to obtain an accurate vascular wall size. Also, it is possible to accurately measure the thicknesses between the inner and outer walls and thus, greater stability of a stent used in all sites (brain, heart, lower limb, etc.) of the human body can be obtained by selecting and using a stent with an accurate size, even upon operation of the stent in the blood vessel.

DISCLOSURE OF INVENTION

Technical Problem

The present invention has been conceived in accordance with the above-described technical background, and an object of the invention is to provide a method capable of imaging both the inner and outer walls of the blood vessel.

Another object of the present invention is to provide a method capable of imaging both the vascular inner and outer walls by an magnetic resonance imaging system to automatically divide them.

Technical Solution to Problem

In order to achieve the above-described objects, the present invention provides a method for acquiring an image where the vascular walls are automatically divided by obtaining two MRI images that reflect different properties of the blood vessel and obtaining the difference between the two images.

That is, the method for acquiring MRI images according to one aspect of the present invention comprises the steps of: obtaining a first magnetic resonance image that reflects a first property of a blood vessel; obtaining a second magnetic resonance image that reflects a second property different from the first property; and subtracting the second magnetic resonance image from the first magnetic resonance image.

The method for acquiring MRI images according to another aspect of the present invention comprises the steps of: obtaining a first magnetic resonance image that reflects a first property of a blood vessel; obtaining a second magnetic resonance image that reflects a second property different from the first property; obtaining a third magnetic resonance image by inverting the first magnetic resonance image; and subtracting the second magnetic resonance image from the third magnetic resonance image.

The first and second properties of the blood vessel may include one selected from the group consisting of: a form or thickness of the vascular membranes constituting the blood vessel, a form of the vascular inner wall, a form of the vascular outer wall, and the blood flow.

Here, the first magnetic resonance imaging may be a CISS (Constructive Interference in Steady State) T2/T1 weighted imaging, and the second magnetic resonance imaging may be a T2-weighted imaging.

Advantageous Effects of the Invention

In the automatically divided vascular wall images obtained by using the method for acquiring MRI images according to the embodiments of the present inventions, both vascular inner and outer walls can be imaged, thereby obtaining the thickness between the vascular inner and outer walls.

This corresponds to a source technology which can accurately measure a vascular structure in the head site of the human body. As the accurate measurement result can be thus obtained, it is possible to stably perform an operation utilizing an accurately sized stent during the stent operation. Furthermore, using the above-described techniques, it is possible to accurately measure all vascular structures, such as blood vessels of the head site, as well as cardiovascular structures, such as blood vessels of the lower limbs. Additionally, it is possible to obtain stability for a stent operation at each site.

BRIEF DESCRIPTION OF THE DRAWINGS

FIGS. 1(a)-1(c) shows MRI images with different properties, which represent TOF Angiography, T2 weighted, CISS T2/T1 weighted images with respect to the head area.

FIGS. 2(a)-2(c) shows partial enlarged vascular images of the MRI images with different properties of FIGS. 1(a)-1(c).

FIG. 3 is a flow chart representing the method for acquiring vascular wall images according to an embodiment of the present invention.

DETAILED DESCRIPTION FOR CARRYING OUT THE INVENTION

Hereinafter, preferred embodiments of the method for acquiring vascular wall images through the magnetic resonance imaging system according to the present invention are described in detail with reference to the accompanying drawings. However, description concerning well-known functions and configurations which can make the subject matter of the present invention unnecessarily vague will be omitted.

The configurations of the MRI system as applied to the present invention are widely known in the art and so the description thereof is omitted.

FIGS. 1(a)-(c) shows MRI images with different properties, wherein (a), (b) and (c) respectively represent TOF Angiography, T2 weighted, and CISS T2/T1 weighted images with respect to the head area. FIGS. 2(a)-2(c) shows images which enlarge the vascular parts. Further, the figures attached to the present specification represent the images acquired from the head part of a normal subject using a clinical 3.0 Tesla magnetic resonance imaging device.

TOF Angiography, which measures the blood flow of veins and arteries in the human body using a MRI device and then render them as images, utilizes the blood flow rate, i.e., a property according to TOF (time of flight), using a T1 weighted imaging of the blood flow. TOF Angiography can present in detail a variety of vascular structures of individual patients with excellent image resolution. Accordingly, TOF Angiography is one of the most common vascular imaging techniques that are currently used in the medical field. Furthermore, as related medical techniques continue to develop, complex blood flow phenomena such as turbulence can also be diagnosed. In recent years, microvascular image can be obtained. As such, the speed of development thereof is fast. Accordingly, TOF Angiography is known to be the most suitable method to obtain overall imaging of the blood vessel, but there is a probability that the blood flow rate could be changed by the vascular inner wall structure, and as a result of which, all of the structures of the vascular inner and outer walls could not be entirely identified.

The T2 weighted images represent a transverse attenuation due to T2 relaxation by the impact between the spindles and this can be used to measure the thickness of the tunica adventitia.

CISS (Constructive Interference in Steady State) T2/T1 weighted images can image a tunica media site of the blood vessel and at the same time measure the signal of the blood flow.

Figure 4:
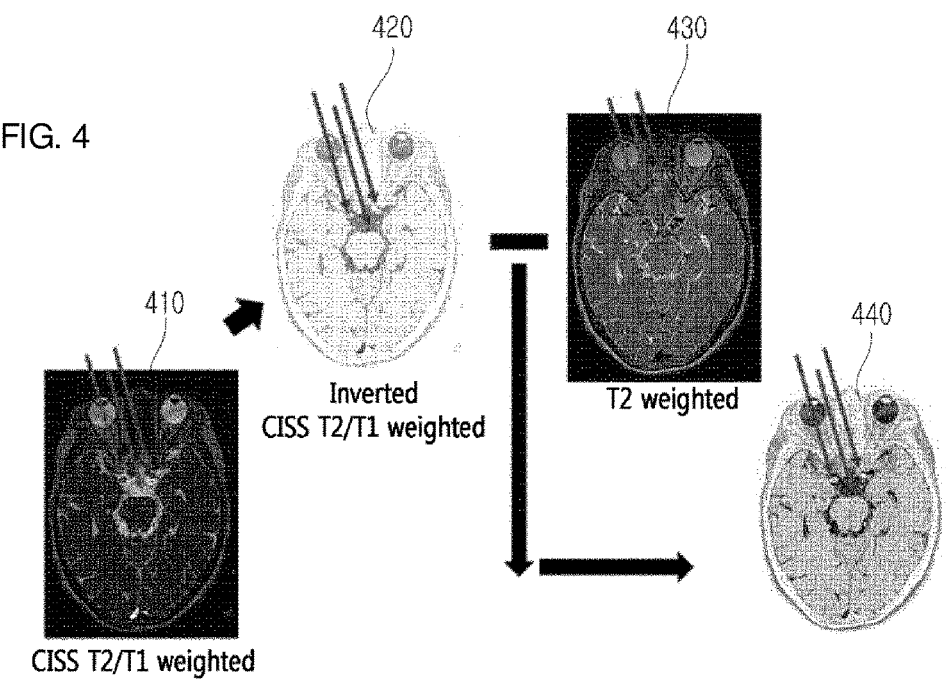
FIG. 4 shows images treated according to the method for acquiring vascular wall images according to an embodiment of the present invention.

FIG. 3 is a flow chart representing the method for acquiring vascular wall images according to an embodiment of the present invention. FIG. 4 shows images treated according to the method for acquiring vascular wall images according to an embodiment of the present invention.

As shown in FIG. 3, CISS T2/T1 weighted imaging (410) is acquired (S310), and this image is allowed to invert, thus obtaining an inverted image (420) (S320).

Next, separately acquired T2 weighted image (430) is subtracted from the inverted CISS T2/T1 weighted image (420), thereby obtaining an image (440) where the vascular walls are automatically divided.

Figure 5A:
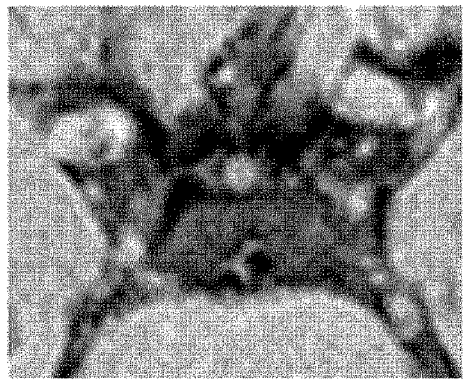
FIGS. 5(a)-5(b) shows enlarged images of the images treated according to the method for acquiring vascular wall images according to an embodiment of the present invention.
Figure 5B:
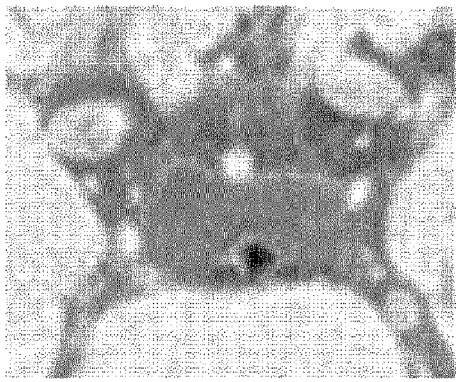

FIGS. 5(a)-5(c) shows enlarged images of the images treated according to the method for acquiring vascular wall images according to an embodiment of the present invention.

FIG. 5(a) represents a tunica adventitia, and FIG. 5(b) represents a tunica media.

As shown in FIGS. 5(a)-5(c), simply subtracting a T2 weighted image from two MRI image, that is, from the inverted CISS T2/T1 weighted image (420), can obtain an accurate structure including the vascular inner and outer walls, and an accurate measurement is possible without any element influencing the vascular structure, for example, the blood flow rate being changed by the vascular inner wall structure or a catheter being inserted into the blood vessel for the administration of a contrast media.

The above-described embodiments illustrate that an image where vascular walls are automatically divided is obtained by inverting the CISS T2/T1 weighted image therefrom and subtracting T2 weighted image from the inverted CISS T2/T1 weighted image, but the two MRI images that reflect different properties of the vascular outer and inner walls are not always limited to the above two. Specifically, if the difference between the image capable of representing a contour of the vascular outer wall and the image capable of representing a contour of the blood flow and the vascular inner wall can be obtained, it is possible to obtain a similar effect. That is, the two images used may be images which include one selected from the group consisting of: the form or thickness of the vascular membranes constituting the blood vessel, the form of the vascular inner wall, the form of the vascular outer wall, and the blood flow. For example, the above advantages can be accomplished even by a combination of T1 image and T2 image, Proton image and T1 image, Proton image and T2 image, T1 image and T2* image, Proton image and T2* image, and the like.

Two MRI image used to obtain the automatically divided vascular wall images can be obtained by any manner or order. However, obtaining the images at a similar time would be advantageous to obtain an accurate result.

Although the forgoing is described with reference to the preferred embodiments of the present invention, it will be appreciated by those of ordinary skill that various changes and modifications can be made to the present invention without departing from the sprit and scope of the invention as set forth in the claims below.

What is claimed is:

1. A method for acquiring a vascular wall image, which comprises the steps of:
obtaining a first magnetic resonance image of a first type, the first magnetic resonance image reflecting a first structural property of a blood vessel;
obtaining a second magnetic resonance image of a second type that is different from the first type, the second magnetic resonance image reflecting a second structural property of the blood vessel that is different from the first structural property;
determining a difference between the second structural property of the second magnetic resonance image and the first structural property of the first magnetic resonance image; and
providing the vascular wall image based at least on the difference between the second structural property of the second magnetic resonance image and the first structural property of the first magnetic resonance image.

2. The method for acquiring MM images according to claim 1, wherein the first and second structural properties include one selected from the group consisting of: a form or thickness of a vascular membrane constituting the blood vessel, a form of the vascular inner wall, a form of the vascular outer wall, and a blood flow.

3. The method for acquiring MM images according to claim 1, wherein the first magnetic resonance image is a CISS (Constructive Interference in Steady State) T2/T1 weighted image.

4. The method for acquiring MM images according to claim 1, wherein the second magnetic resonance image is a T2-weighted image.

5. A method for acquiring a vascular wall image, which comprises the steps of:
obtaining a first magnetic resonance image of a first type, the first magnetic resonance image reflecting a first structural property of a blood vessel;
obtaining a second magnetic resonance image a second type that is different from the first type, the second magnetic resonance image reflecting a second structural property of the blood vessel that is different from the first structural property;
obtaining a third magnetic resonance image of a third type by inverting the first structural property of the first magnetic resonance image;
determining a difference between the second structural property of subtracting the second magnetic resonance image and the first structural property of the third magnetic resonance image; and
providing the vascular wall image based at least on the difference between the second structural property of the second magnetic resonance image and the first structural property of the third magnetic resonance image.

6. The method for acquiring MM images according to claim 5, wherein the first and second structural properties include one selected from the group consisting of: a form or thickness of a vascular membrane constituting the blood vessel, a form of the vascular inner wall, a form of the vascular outer wall, and a blood flow.

7. The method for acquiring MM images according to claim 5, wherein the first magnetic resonance image is a CISS (Constructive Interference in Steady State) T2/T1 weighted image.

8. The method for acquiring MM images according to claim 5, wherein the second magnetic resonance image is a T2-weighted image.

9. A method for acquiring a vascular wall image, which comprises the steps of:
obtaining a first magnetic resonance image of a first type, the first magnetic resonance image reflecting a first structural property of a blood vessel;
obtaining a second magnetic resonance image of a second type that is different from the first type, the second magnetic resonance image reflecting a second structural property of the blood vessel that is different from the first structural property;
obtaining a third magnetic resonance image of a third type by inverting the first structural property of the first magnetic resonance image;
determining a difference between the second structural property of the second magnetic resonance image and the first structural property of the third magnetic resonance image; and
providing the vascular wall image based at least on the difference between the second structural property of the second magnetic resonance image and the first structural property of the third magnetic resonance image,
wherein the first magnetic resonance image is a CISS (Constructive Interference in Steady State) T2/T1 weighted image, and
wherein the second magnetic resonance image is a T2-weighted image.

* * * * *

UNITED STATES PATENT AND TRADEMARK OFFICE
CERTIFICATE OF CORRECTION

PATENT NO. : 10,420,485 B2
APPLICATION NO. : 15/319150
DATED : September 24, 2019
INVENTOR(S) : Jun Young Chung et al.

It is certified that error appears in the above-identified patent and that said Letters Patent is hereby corrected as shown below:

In the Claims

In Claim 2, Column 5, Line 20:
"MM" should read --MRI--.

In Claim 3, Column 5, Line 26:
"MM" should read --MRI--.

In Claim 4, Column 5, Line 30:
"MM" should read --MRI--.

In Claim 5, Column 5, Line 47:
"property of subtracting the second magnetic resonance" should read --property of the second magnetic resonance--.

In Claim 6, Column 6, Line 7:
"MM" should read --MRI--.

In Claim 7, Column 6, Line 13:
"MM" should read --MRI--.

In Claim 8, Column 6, Line 17:
"MM" should read --MRI--.

Signed and Sealed this
Fifth Day of October, 2021

Drew Hirshfeld
*Performing the Functions and Duties of the
Under Secretary of Commerce for Intellectual Property and
Director of the United States Patent and Trademark Office*